United States Patent [19]

Svedman

[11] 4,382,441
[45] May 10, 1983

[54] DEVICE FOR TREATING TISSUES, FOR EXAMPLE SKIN

[76] Inventor: Pál Svedman, Sibbarpsvägen 47 A, S-216 11 Malmö, Sweden

[21] Appl. No.: 200,501
[22] PCT Filed: Dec. 6, 1979
[86] PCT No.: PCT/SE79/00246
§ 371 Date: Aug. 6, 1980
§ 102(e) Date: Aug. 5, 1980
[87] PCT Pub. No.: WO80/01139
PCT Pub. Date: Jun. 12, 1980

[30] Foreign Application Priority Data

Dec. 6, 1978 [SE] Sweden .............................. 7812541

[51] Int. Cl.³ .......................................... A61M 37/00
[52] U.S. Cl. ..................... 604/291; 604/114; 604/305
[58] Field of Search ..................... 128/1 R, 82, 207.19, 128/207.26, 248, 254, 260, 325, 334 R, 803, 132 R, 155

[56] References Cited

U.S. PATENT DOCUMENTS

| 603,815 | 5/1898 | Duke | 128/803 |
| 3,026,874 | 3/1962 | Stevens | 128/260 |
| 3,288,140 | 11/1966 | McCarthy | 128/248 |
| 3,486,504 | 12/1969 | Austin, Jr. | 128/300 |
| 3,610,238 | 10/1971 | Rich, Jr. | 128/132 R |
| 3,765,414 | 10/1973 | Arlen | 128/260 |
| 3,874,387 | 4/1975 | Barbieri | 128/325 |
| 3,896,806 | 7/1975 | Wichterle | 128/260 |

FOREIGN PATENT DOCUMENTS

| 2809828 | 9/1978 | Fed. Rep. of Germany | 128/248 |
| 641061 | 8/1950 | United Kingdom | 128/132 R |

OTHER PUBLICATIONS

"Local Hyperalimentation of Open Wounds", Jouko Viljanto and Jyrki Raekallio, Br. J. Surg., vol. 63 (1976), 427-430.

Primary Examiner—Lee S. Cohen
Attorney, Agent, or Firm—Ostrolenk, Faber, Gerb & Soffen

[57] ABSTRACT

The device comprises a dressing made from a porous material (11) intended for placing against tissues, for example skin, the material being synthetic or organic and being distinguished by communicating cavities in the form of open pores, interdigitating gaps in particle material or communicating cavities in capillary structures. The dressing (11) can, by layers, have different cavity qualities and is provided with a dense, sealing shell (10) or layer in which is disposed at least one fluid supply connection (12) and at least one fluid removal connection (13) in spaced apart relationship. Conduits are coupled to the connections (12, 13) and permit the establishment of treatment fluid flow from the supply connection (12), through the cell material dressing (11) in contact with the tissue, to the removal connection (13). Fluid supply can be effected under pressure and/or fluid removal under suction. Electrodes can be disposed in the cell material dressing (11) for sensing the fluid saturation degree, and with the possibility of registering and/or regulating this saturation degree by means of valves. Temperature sensors may be provided in the supply conduit or in the cell material dressing (11) and may be connected to a temperature regulator. Fluid-impervious walls may be provided in the cell material dressing (11) for guiding the treatment fluid flow. The cell material dressing may have one or several replaceable layers.

18 Claims, 5 Drawing Figures

DEVICE FOR TREATING TISSUES, FOR EXAMPLE SKIN

The present invention relates to a device for treating tissues, for example skin, comprising a porous material intended to abut against the tissue and a fluid-impervious shell or layer which covers at least some of the material.

The object of the present invention is to realize a device which makes possible a considerably more easily handleable and, for the patient, more comfortable device for treating ulcers and skin injuries or the like, which entails rapid healing under conditions which are safe with regard to the risk of infection. This object is achieved by means of a device which is characterised in that the porous material consists of at least one cell material with open pores, and that the shell or layer has at least one connection for fluid supply and at least one connection for fluid removal in spaced apart relationship, in order, by means of conduits coupled to the connections, to establish a treatment fluid flow from the supply connection, through the cell material in contact with the skin, to the removal connection.

The invention will be described in greater detail below with reference to accompanying drawings which schematically illustrate embodiments of the invention.

Figure 1:
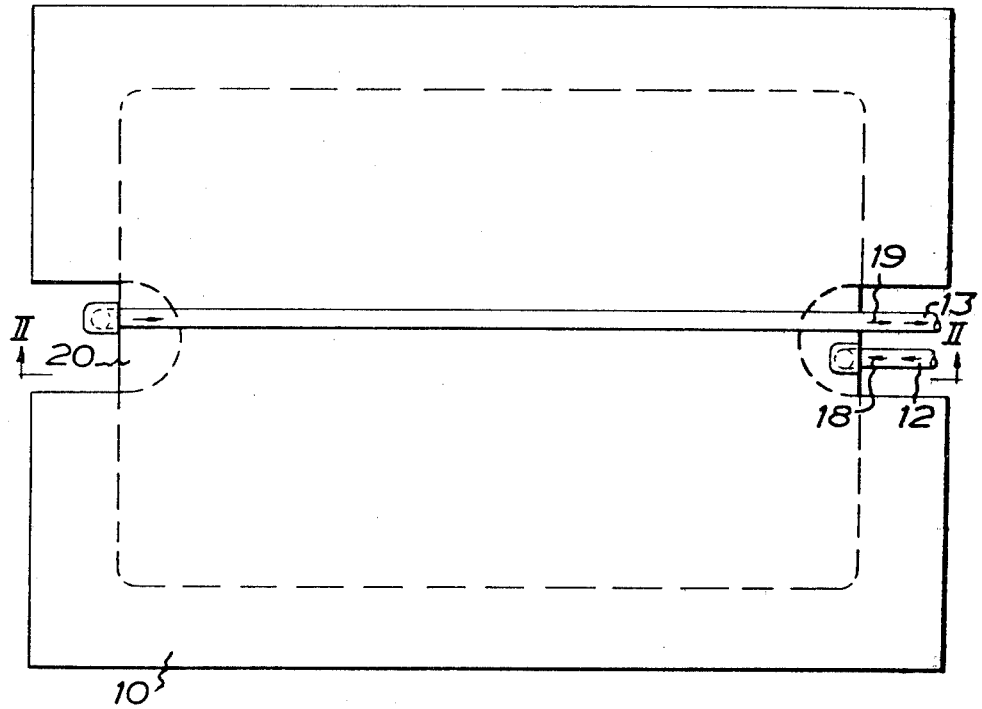
FIG. 1 is a top plan view of a simple embodiment of the invention.
Figure 2:
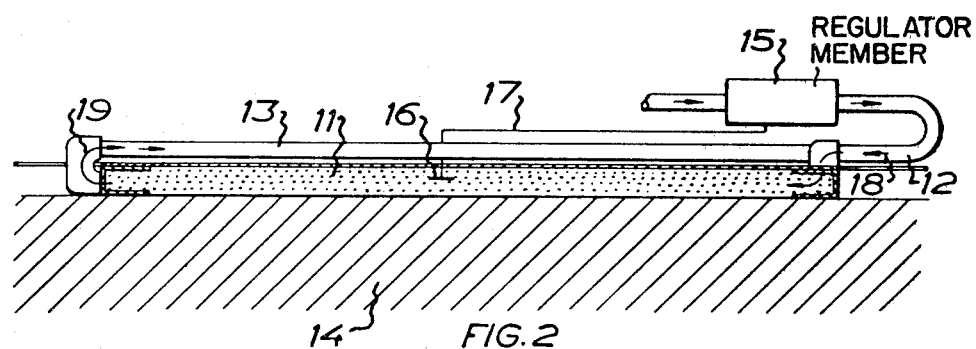
FIG. 2 is a section taken along the line II—II in FIG. 1.

The device according to the invention consists of a cell material dressing 11 with a communicating cavity system and a covering shell or layer 10 of fluid-impervious material. The shell 10 has at least one fluid supply connection 12 and at least one fluid removal connection 13. Thus, fluid can be supplied by the intermediary of the connection 12, as illustrated by means of arrows 18, and be caused to flow through the cell material dressing 11 and be removed via the connection 13, as shown by means of arrows 19. In order to facilitate fluid passage through the cell material, the fluid can be supplied under pressure and/or be removed by suction. In the supply conduit, there is coupled a regulator member 15 which accommodates a valve means and means for cooling and/or heating the fluid which is supplied to the cell material. A sensor 16 which is arranged to sense fluid saturation in the cell material, is placed therein and connected to the valve means of the regulator member 15 by a conduit 17. Fluid-impervious members 20 are disposed at the transitions of the connetions 12, 13 into the cell material in order to guide the flow.

The cell material dressing 11 constitutes a cavity system in the form of cells with open pores or communicating capillary systems, or consists of particles with interposed communicating gaps. The material can be synthetic, e.g. consist of polyurethane or similar plastics material, or may consist of regenerated cellulosic fibres with a binder of, for example, polyester polyamide on fabric. The material may consist of sponge or rubber or contain another type of elastic component. The structure can also be realized by overlaid particles of small size of plastics/glass/ceramics or the like. Organic compounds may be basic materials, for example cellulosic fibres of e.g. dextran polymer particles cross-linked with epichlorohydrin (Sephadex-Debrisan, possibly with glycerin or the like as binder). If particles are used as material, it may be practical to utilize continuous layers with open pores adjacent the skin or tissue layer which is to be treated.

The material can be inert with respect to chemical substances, biological particles and bacteria. The cell material may contain chemical compounds which reversibly bond, for example, water molecules and which thus actively contribute to the fluid suction capacity. The material can contain compounds which act as catalysts on the treatment effects.

The formed cavity system may be of random disposition or have a preferential major direction. This latter permits guiding the treatment fluid flow. Guiding can also be provided in the pore system by walls which are impermeable to the treatment fluid.

The cavity system may, in layers, have different diameters. Such layers may be structurally different from each other and be replaceable, or structurally megre in each other. One layer may consist of a continuous material and the superjacent layer of particles. Conceivably, the material may be denser in one region and looser in another with a gradual transition. Commercially, materials of different cavity characteristics are available.

For certain fields of use, the material needs to be pliable, soft and mouldable, for others a firmer possibly rigid structure is advantageous. The walls are made accordingly, soft to hard, possibly with an elastic component, or rigid. The material can, for example, be cut to suitable format according to certain basic material sizes. Such material can be shaped according to a part of the body. For example, the shell or layer 10 can be cupped to make it possible to apply particles between the part of the body and the shell. The porous material surface can be provided with adhesive regions for fixing against adjacent surface layers which are to be treated. As regards the material surface, this should, on its side facing the surface layer which is to be treated, have pores, spaces or capillary systems which establish contact between the surface layer and the cavity system.

The shell or layer 10 can cover larger or smaller parts of the cell material dressing 11. The shell 10 may be manufactured of, for example, plastics, glass, rubber or other rigid material or consist of a fluid-tight surface layer on the cell material dressing 11. The shell should have a surface tension distributing effect and influence the passage of liquid. The shell 10 also contributes to directing the suction effect or pressure effect in the material and to retaining fluid in place in the material. The shell 10 may have a greater surface area than the cell material so as to make possible abutment against the skin. The shell 10 may possibly be fixed in the porous material at only one or at several localized regions and can be a separate unit intended for application above a certain cell material with one or more adhesion points. Furthermore, the shell 10 may be provided with insulation to reduce heat losses into the ambient atmosphere. Suitably, the supply and removal conduits 12, 13 are then also insulated.

The cell material dressing 11 and shell 10 must, for application to humans, be pliable, soft as regards application on irregular ulcerations (see below). As regards application on regions where the skin is intact, a stiffer structure may be advantageous.

The device according to the invention has at least one fluid supply connection (e.g., a pipe) 12 and at least one fluid removal connection (e.g., a pipe) 13 which are located at a predetermined distance from each other. Factors of importance in determining the suitable mutual spacing are, int.al. the type of treatment fluid, capillary activity, cavity and wall characteristics and the applied pressure/suction. The connections 12, 13 can be designed in different ways. According to one alternative, each connection is formed of a ring of the shell material. The connections can also comprise holes in the shell 10, possibly distributed with suitable spacing, permitting the adaptation of material of standard size to treatment areas of different sizes. The connections 12, 13 can be placed in different parts of the cell material with respect to the layer which is to be treated and can, furthermore, be movable by means of a simple retention device. The connections can, furthermore, be countersunk in the shell or cell material and be coupled direct or via intermediate connecting pieces to extant conduits. The connections 12, 13 may have passages in their walls where they are in contact with the porous material. The connection conduits can also branch out in the cell material and are suitably reinforced to prevent "throttling" or collapse under suction. The pressure or suction effect can be directed in the cell material by means of one or more walls in the connection regions thereof. Each unit can have several fluid supply connections and fluid removal connections.

The supply and removal conduits can be coupled in an intermediate coupling piece for manual connection to a supply and removal assembly such that the patient himself can start the device and the treatment and discontinue this process e.g. in order to be able to get out of bed. This entails that the system places no great demands on personnel. Several material units, each one possibly with several connections for pressure/suction, can conceivably be interconnected so that supply of fluid at a certain pressure and/or discharge flow at a certain suction can be effected by means of one and the same manual or automatic control unit.

In the connection conduits, sensors can be provided for flow and temperature, and manometers with a possibility for manual or automatic registration and regulation.

Devices for preventing back flow may be provided, as can filters. The supply flow is most simply effected by the intermediary of a drip bottle and discharge flow by means of vacuum suction. Automatic drip chambers or the possibility for automatically placing the supply flow under a certain pressure may be provided in accordance with known medical technology.

It is practical to apply a sensor 16 in the cell material in order to sense the degree of fluid saturation. This sensor may be based on the principle that the impedance between two electric conductors changes when the liquid concentration between the conductors is altered. The terminal conductor 17 of the sensor 16 comprises wires, and a small regulator unit with a battery as alternative power supply permits registration and, after calibration, automatic regulation of the degree fluid saturation by coupling to the valve means of the regulator member 15. A temperature sensor may be disposed in the cell material and may be connected to the means of the regulator member 15 for cooling or heating the fluid.

The device according to the invention permits distribution and demarcation of treatment fluid within a determined area, regulatable treatment fluid flow and regulatable pressure/suction effect. Treatment effects are distributed through open pores vis-à-vis other fluid, other phases or solid material in accordance with the following operational example.

On use of the device for, for example, ulcer treatment, the free surface of the cell material dressing 11 facing away from the shell or layer 10 is applied to the tissue which, in FIGS. 2-5, is designated 14, and the ulcer in the tissue.

Figure 3:
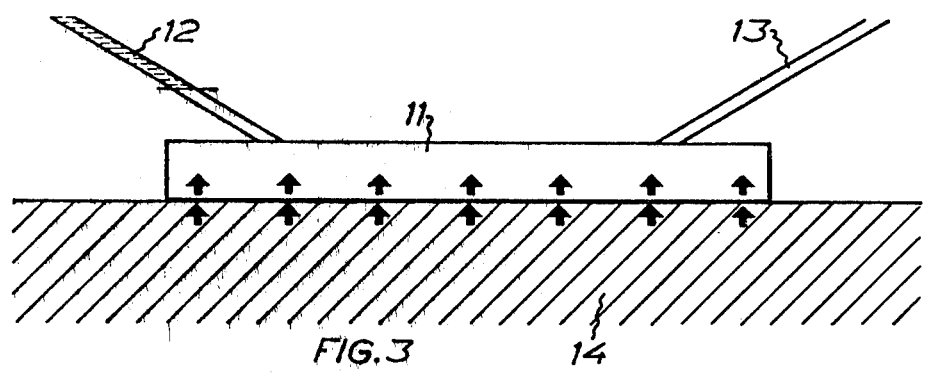
FIGS. 3, 4 and 5 show the device in operation and illustrate how the device works on treatment of a tissue.
Figure 4:
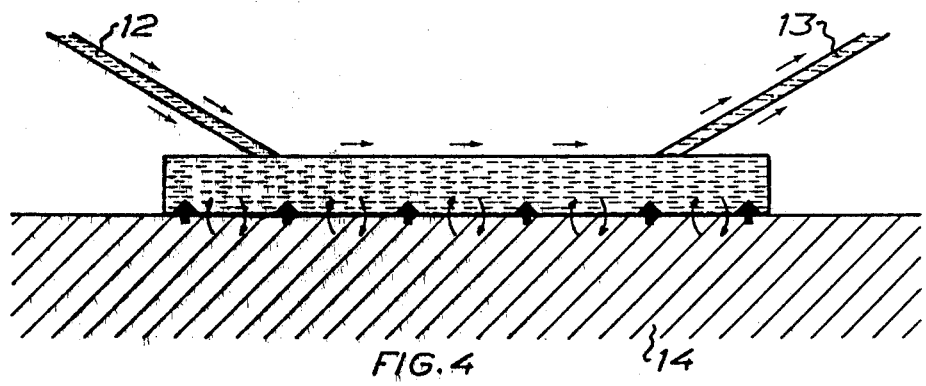
Figure 5:
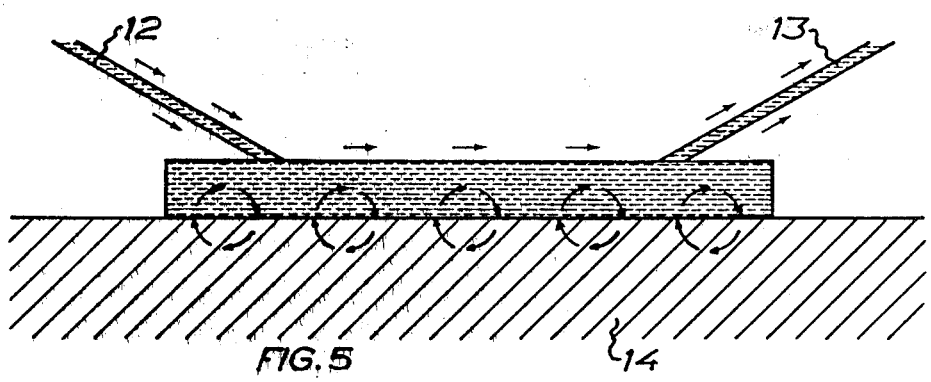

Liquid which is supplied to the cell material 11 will, because of the material structure, be distributed in and restricted to the material in accordance with laws of physics concerning surface tension and capillarity. The sphere of effects embraces liquid molecules, air (gas) and molecules in the wall material. In the material, conceivable states are from no wetting up to complete wetting as shown in FIGS. 3-5. The wetting or saturation degree is related to the quantity of capillarily functioning pores. The state which is to be striven for is that which entails the same degree of wetting throughout the entire material.

If there are capillarily functioning, open pores in the cell material 11 facing that area of skin 14 which is to be treated, the material will have a certain absorptive force distributed throughout the material surface. The absorptive force will be related to the degree of wetting in the material and to a possible partial vacuum if suction is exercised in the discharge connection 13. The fluid flow in the material is influenced inter alia by applied pressure or suction and by capillary forces. As a result of pressure/suction influence, the major direction of the fluid flow will be from the supply to the removal connection. Within the different parts of the cell material, the flow direction will be determined by differences in the liquid saturation in adjacent material regions. The liquid will be moved in that direction where liquid saturation is lowest and where, consequently, capillary force is greatest. Substances which are sucked up in the material from adjacent tissue will pass towards regions where liquid saturation is lowest and, finally, towards the discharge suction. If the material is inert, the continuous treatment fluid flow will render the system self-purifying as regards contamination by molecules and particles in the size range up to pore/space or capillaries. The treatment fluid flow and sucking-up from the surface layer result in the removal of contaminants from the treatment surface. The sorption process which may be influenced by different liquid saturation degrees, and the described passage of substance with the fluid constitute, together with the chemical effects described below, considerable advantages in the invention.

The treatment fluid in the material will, as a result of its chemical composition, be able to influence the composition in adjacent skin layers and vice versa. Since a flow of treatment fluid is a precondition, chemical equilibrium will not be reached. Diffusion and concentration gradients control the exchange on the molecular level between treatment fluid and the tissue layer being treated. Differences in the osmotic pressure between treatment fluid and surface layer can be utilized for achieving a distribution effect. The inflow of liquid permits viscosity change in adjacent surface layers.

By regulating the fluid saturation degree in the material, it is possible to a certain extent to control the chemical effects. Regulation of fluid temperature and fluid flow rate permit tempering of the treated surface.

Two material layers, possibly with different treatment fluid characteristics according to the invention may permit added influence of each other independent of regulation possibilities.

Treatment fluid is adapted with regard to type, and, by means of additives, to the contemplated goal of treatment under consideration of the above-outlined, possible influences. It is conceivable to influence the liquid sucking of the sytem by using a capillary-active fluid or by the addition of suitable capillary-active substance.

A gas may be distributed in the cell material, its direction of flow being determined partly by applied pressure or suction, partly in accordance with possible preferential pore direction or controlled by possible fluid-impervious walls. Excess pressure in the material entails gas conveyance to the skin or the tissue and partial vacuum entrails suction therefrom.

Operational Example

A. Application to ulcerations (skin damage with tissue loss)

Local treatment at the clinic is effected by means of ointment dressing, wet or dry, possibly tempered dressing, washing or removal by suction of secretions by means of special dressings. Substances of importance for healing are added, antibiotics, bactericides, enzymes for the degradation of dead tissue etc.

In itself, the invention constitutes a capillary system with certain similarities to the transport system which supplies the cells of the tissue with nutritive substances and removes degradation products. The invention provides the following treatment possibilities: supply of nutritive substances, oxygen, enzymes for the degradation of nectrotic material, the supply of antibiotics, the supply of liquid at optimum pH, the supply of medicaments with particular ulcer effects (zinc, vitamin A etc.). Osmotically active solutions can be supplied. Bacteriostatic or bactericidic solutions may also come into question. The ulcer may quantitatively be hydrated by the assistance of the device according to the invention, and difussion of treatment agent can, to a certain extent, be controlled. The ulcer wound can be tempered (heat/cooling). Collections of tissue liquid can be removed as a result of the continuous suction effect of the device. The system is self-purifying. As opposed to conventional dressing treatment, regular changes of dressing have proved to be unnecessary. The risk of infection in conjunction with dressing change is hereby reduced. Contaminant articles of a diameter which is greater than the pores of the material can be absorbed against the treatment side of the material and be removed when the material is taken off. In cases of particularly secretive ulcers, it has been possible to change the inner layer of pore material, for example, twice daily, while the outer layer with connections is retained for from one to two days.

Oxygen gas can be supplied, for example, in two layer systems in which the oxygen gas flow is introduced outside a liquid flow adjacent the ulcer. If the inner layer is moderately hydrated, the passage of gas is permitted to the base of the ulcer. Liquid contact prevents, at the same time, drying out. One advantage is that the porous material is inert and is not absorbed into the body. The risk of allergy is minimal.

Compared with conventional treatment, the device according to the invention is very simple to manage and requires fewer personnel. The patient himself can couple in the device. The environment in the ulcer can continuously or intermittently by supplied with different doses of treatment agent. The device can be used when the patient is ambulant. Mediccal care personnel then apply the cell material with suitable support dressing and an intermediate connecting piece accessible to the patient for connection to the flow conduits. Apart from this, it is required of the patient that he be capable of managing a drip bottle and manual suction assembly. The gains involved in such therapy may be seen in relation to the heavy care costs involved for in-patients.

B. Local treatment of burn injuries to skin

According to conventional local treatment of burn injuries, a dressing is applied, possibly with a liquid absorption capacity (Epigard, Debrisan). The surface is treated with bactericides or bacteriostatic substances or antibiotics. The body is tempered by initial cooling and, later in order to counteract excessive energy losses, heating.

All effects can be provided and dosed by means of the device according to the invention. Burn injuries caused by chemical agents can, according to the invention, rapidly be diluted with antidote, and injurious substances be sucked out of the skin.

C. Application to soft part injuries (inflammation) or fractures with unbroken skin Local tempering of injured tissue is used as therapy and similarly antiphlogistic substances.

According to the invention, a determined temperature effect can be imparted to an injured part of the body. At the same time, antiphlogistic substances can be added to the treatment fluid which, after skin passage (see D) further alleviates the reaction.

D. Application to eczema in various phases of inflammation or infection

Local treatment according to conventional methods as disclosed under A may be topical. Often however, use is made of occlusion treatment. This treatment comprises a hydrated dressing with a treatment agent and a sealing material overlaid on the outside. Hydration of intact skin increases the possibilities of diffusion of the treatment agent many times over. Passage out of the skin is also facilitated.

The device according to the invention, with adapted treatment fluid, permits continuous and regulated hydration of the skin with the above-disclosed increase of the diffussion possibilities for an added treatment agent—agent which can be replaced by further supply flow according as it is consumed. Liquid flow and suction effect also have a purifying influence in that the infective substance, inflammation mediators, degradation products and oedema are removed.

E. Cosmetic aplications (1) According to conventional therapy, use is made, in the treatment of acne, of antibiotics and radiation with heat effect. The invention is employed with the application of a face mask, possibly with tempering and an addition of antibiotics or antiphlogistic substances to the treatment fluid.

(2) Use in cosmetic indication so as to provide passage of liquid and molecular substances through the skin into and out of the tissue, for example in the cosmetic treatment of aging skin (face mask). Localized heating/cooling of the skin also provides a potential application in modifying the blood circulation through the skin for so-called vitalization purposes.

F. Other fields of application

Application against bacteria or cell growth substrate which makes possible a continuous, optimum supply of growth substances, replacement of substrate substances and removal of the degradation product. Tempering of the environment. Conventional technology does not allow for these effects.

A device permitting viability maintenance treatment of skin/tissue in vitro.

The device according to the invention can also be used in industrial and biological contexts, for example as a component in an electrophoresis system or in plant cultivation, in which latter case the cell material 11 with associated shell 10 is in the form of a large material unit in, for example, a greenhouse and functions as a surrogate for earth, nutritive substances for plants of different types being added. The plants take root in the porous system of the material. A looser top surface of the material improves the possibilities for taking root. Regulator means for different nutrition components are conceivably based in the material. The treatment fluid flow in the system may also be influenced in that the inclination of the material unit is varied.

The invention permits continuous dosage of water, fertilizer and nutritive substances. No loss need be suffered of these substances as a result of percolation, because the shell is impermeable. The system precludes the risk of contamination of the ground water with agricultural chemicals. Possibly, the flow can be directed by means of furrow-forming material in which the plants are placed, with intermediate portions of capillarily active material. As a result, the quantity of requisite nutritive substances which does not have direct contact with the plants is reduced.

I claim:

1. A device for treatment of tissue, comprising:
   a dressing formed of a porous material having first and second opposed major surfaces;
   said first major surface being exposed;
   a fluid supply pipe delivering fluid supplied thereto directly to only a first portion of said dressing;
   a fluid removal pipe directly receiving fluid exiting said dressing at a second portion of said dressing only, said second portion being spaced from said first portion;
   the internal structure of said dressing causing fluid entering said fluid supply pipe to migrate from said first portion to said second portion of said dressing as a result of the capillary action of said porous material.

2. A device according to claim 1, wherein said first and second portions are at opposite ends of said dressing.

3. A device according to claim 2, wherein said first and second major opposed surfaces are substantially planar and parallel to each other and wherein said fluid migrates in a direction substantially parallel to said surfaces.

4. A device according to any one of claims 1, 2 or 3, further including means for introducing fluid into said fluid supply pipe under pressure.

5. A device according to any one of claims 1, 2 or 3, further including means for removing fluid from said fluid removal pipe by suction.

6. A device according to any one of claims 1, 2 or 3, further including means for sensing the degree of fluid saturation in said dressing.

7. A device according to claim 6, wherein said means includes electrodes disposed in said dressing.

8. A device according to claim 6, further including means for registering said second degree of fluid saturation.

9. A device according to claim 6, further including means for regulating the flow of fluid through said dressing as a function of said sensed degree of fluid saturation.

10. A device according to any one of claims 1, 2 or 3, wherein said dressing includes fluid impervious walls for guiding the flow of fluid between said fluid supply pipe and said fluid removal pipe.

11. A device according to claim 1, wherein said dressing includes a replaceable micropore layer defining said first major surface.

12. A device according to claim 1, wherein said dressing comprises at least one cellular material having open pores.

13. A device according to claim 1, wherein when said exposed major surface of said dressing is placed against injured tissue, said dressing influences said injured tissue by sorptive processes.

14. A device according to claim 1, further including means for supplying fluid to said fluid supply pipe and temperature regulating means for regulating the temperature of said fluid before it is supplied to said fluid supply pipe.

15. A device according to claim 14, wherein said temperature regulating means includes sensors disposed in said dressing.

16. A device according to any one of claims 1, 2 or 3, wherein the internal structure of said dressing causes said fluid to distribute through substantially the entire area of said dressing due to capillary action.

17. A device according to claim 1, further including a fluid impervious layer located on said second major surface.

18. A device according to claim 17, wherein said fluid supply pipe includes a first opening formed in said fluid impervious layer and said fluid removal pipe includes a second opening, spaced from said first opening, formed in said fluid impervious layer.

* * * * *